May 4, 1965 F. M. MEDWEDEFF ETAL Re. 25,773

X-RAY FILM HOLDER AND AIMING ELEMENT

Original Filed July 28, 1961 2 Sheets-Sheet 1

INVENTORS
FRED M. MEDWEDEFF
WILLIAM H. KNOX
By
ATTORNEY

X-RAY FILM HOLDER AND AIMING ELEMENT

Original Filed July 28, 1961 2 Sheets-Sheet 2

INVENTORS
FRED M. MEDWEDEFF
WILLIAM H. KNOX
By
ATTORNEY

United States Patent Office

Re. 25,773
Reissued May 4, 1965

25,773

X-RAY FILM HOLDER AND AIMING ELEMENT

Fred M. Medwedeff and William H. Knox, Nashville, Tenn., assignors to Precision X-Ray Company, North Nashville, Tenn.

Original No. 3,092,721, dated June 4, 1963, Ser. No. 127,671, July 28, 1961. Application for reissue Feb. 10, 1964, Ser. No. 354,194
13 Claims. (Cl. 250—70)

Matter enclosed in heavy brackets [ ] appears in the original patent but forms no part of this reissue specification; matter printed in italics indicates the additions made by reissue.

This invention relates to a combined X-ray film holder and aiming element. More particularly, the aiming element portion of the device is adapted to be used with X-ray machines equipped with either short or long and either blunt or pointed cones.

It has been common practice for a long period of time to hold X-ray film within the oral cavity by means of the patient pressing a finger or thumb against the X-ray film to position and hold the same adjacent the gum area to be X-rayed. The dentist or X-ray technician then aims the cone of the X-ray machine, as best he can, toward the gum area which is to be X-rayed, preferably with the axis of the X-ray nose or cone being perpendicular to the plane of the X-ray film plate when using a long cone, or nearly perpendicular thereto as when using the bisect-the-angle technique to be described hereinafter. By using such techniques, it is quite obvious that unless great care is exercised, poor aiming of the nose or cone of the X-ray machine frequently results, whereby the developed X-ray films have images which are distorted such as the teeth appearing longer or shorter than their actual length, or the films are over-exposed in one area and under-exposed in another, root tips are missed by being outside the film area, impressions are fuzzy, other structures such as malar processes in the uppers are superimposed, and the most detrimental aspect of all is that relatively wide areas of facial and gum tissues are unnecessarily subjected to X-rays, in excess of the specific area which will appear upon the developed film and should be the only area subjected to X-rays.

Research in recent years has led substantial segments of the medical profession to believe that unnecessary exposure to X-rays is and can be harmful, and, therefore, is to be avoided. Further, tissues and glands which have not been fully developed, as in young children, can be very decidedly and detrimentally harmed by exposure to certain amounts of X-rays, even very limited amounts sometimes causing damage particularly to such glands as the pituitary and thyroid, notably in children. Accordingly, while X-rays are necessary to aid in many phases of medicine and surgery, these professions now are extensively aware of the need to use X-rays only when and where necessary.

In an effort to improve techniques for taking X-ray image impressions on film, a number of different kinds of holders for X-ray film, some of which have included various kinds of aiming devices, have been devised heretofore. Some of these have had very rudimentary types of aiming devices which do not offer much improvement over the conventional technique of a dentist or technician aiming the cone of an X-ray machine by eye relative to the film held within the patient's oral cavity. In other structures of this type, the same have been provided with means to attach an arm directly to the nose of the X-ray machine, the outer end of the arm having means for holding an X-ray film. Devices of this type frequently do not offer adequate flexibility and convenience for disposing the X-ray film in proper relationship to the gum to be X-rayed, or results in discomfort to the patient and unsatisfactory X-ray impressions on the film.

For purposes of obviating the inherent difficulties of previous techniques and devices and also for aiding a dentist or X-ray technician in taking X-rays of teeth, gums, and the like, with utmost accuracy, it is the principal object of the present invention to provide a relatively simple structure having at one end means to hold one of several types of commonly used X-ray film, and at the other end having both an aiming element, which facilitates the aiming of either long or short and either blunt or pointed nose cones accurately toward the film supported by the holder, and also an X-ray shield. Said shield absorbs and, therefore, prevents X-rays which normally tend to scatter from the principal stream of X-rays from contacting any human tissue, whereby the only X-rays which actually contact such tissues are those which are permitted by design to pass through said shield substantially within an area which substantially is coextensive in shape and size with the X-ray film. This arrangement therefore greatly minimizes possible injury to the patient from any scattered and surplus X-rays contacting human tissue except those tissues which are intended to be subjected to X-rays.

It is another object of the invention to provide within the shield an opening of substantially the same shape and area as that of the X-ray film which is to be subjected to X-rays through said opening in the shield, the holder also holding the X-ray film so as to be substantially parallel to the plane of the shield, and the center of the opening will be substantially coincident with the center of the X-ray film if a line which is perpendicular to the planes of said shield and film is extended between said centers.

A further object of the invention is to provide additional shield members adjustably positionable relative to the opening in the principal shield means in order that the opening through the shield means may be varied to suit certain situations for purposes of minimizing the area to be subjected to X-ray exposure.

Still another object of the invention is to render the shield adjustable relative to the aiming element whereby the opening in the shield means may be arranged to conform with maximum suitability to the position of the X-ray film and particularly rectangular film supported selectively either vertically or horizontally by the holder in opposition to the aiming element and shield.

Details of the foregoing objects and of the invention, as well as other objects thereof, are set forth in the following specification and illustrated in the accompanying drawings comprising a part thereof.

Figure 1:
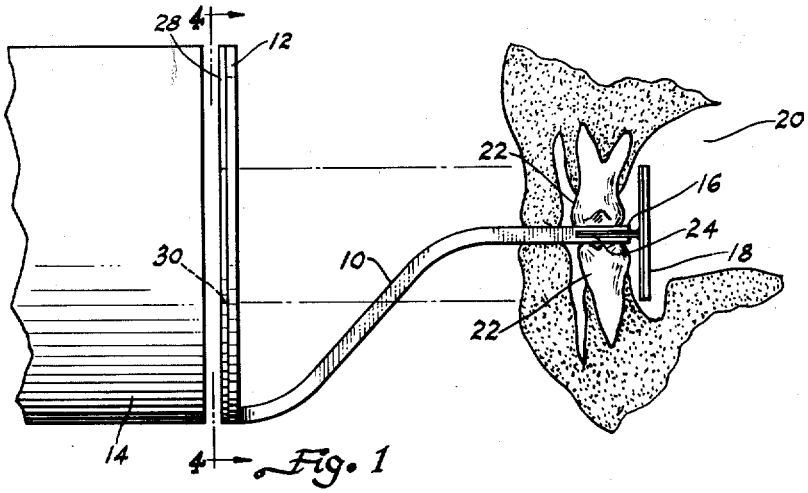
FIG. 1 is a fragmentary side elevation of a combination X-ray film holder and aiming element embodying the principles of the present invention and being illustrated in conjunction with the nose of a long cone X-ray machine, the film holding means in this embodiment being adapted to hold a bitewing type X-ray film.
Figure 3:
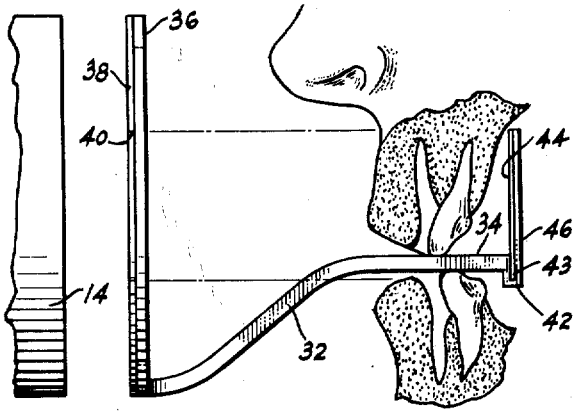

FIG. 3 is a view similar to FIG. 1 but showing, fragmentarily, a slightly different embodiment of X-ray film holder and aiming element being used with a long, blunt cone-type X-ray machine, and the film supporting means being of the type to hold a periapical type of X-ray film adjacent a film support which, if desired, may include a lead sheet to comprise additional X-ray shield means arranged to prevent any X-rays which project through the X-ray film from contacting the interior of the oral cavity.

Figure 2:
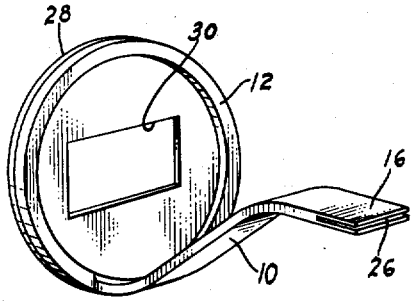
FIG. 2 is a perspective view, looking partially from the rear, of the combination film holder and aiming element illustrated in FIG. 1 but shown on a slightly smaller scale than in FIG. 1.
Figure 4:
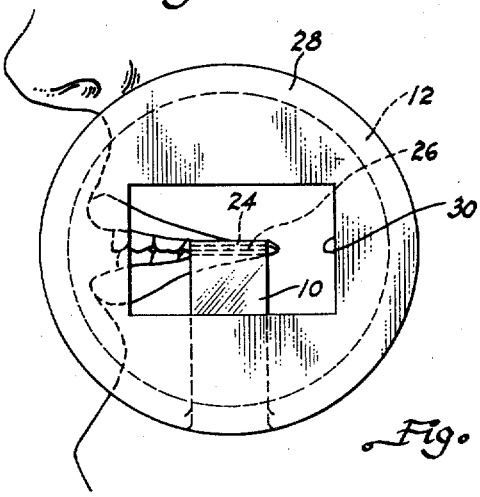

FIG. 4 is a front view of the film holder and aiming element shown in FIGS. 1 and 2 as viewed from the side of a patient's face and presenting a view such as that seen by a dentist or technician incident to aiming an X-ray machine relative to the aiming element to X-ray posterior teeth.

Figure 5:
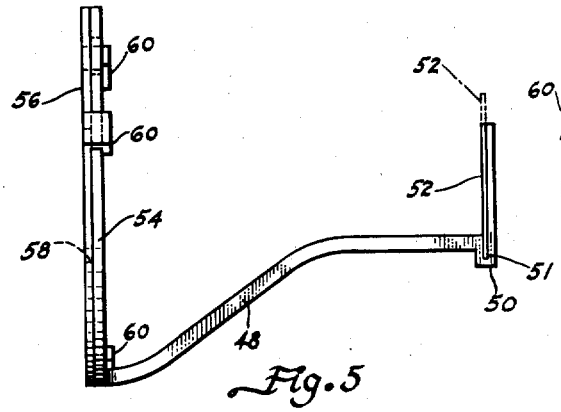

FIG. 5 is a side elevation of still another embodiment of a combination X-ray film holder and aiming element embodying the principles of the present invention as used with an exemplary periapical type of X-ray film.

Figure 6:
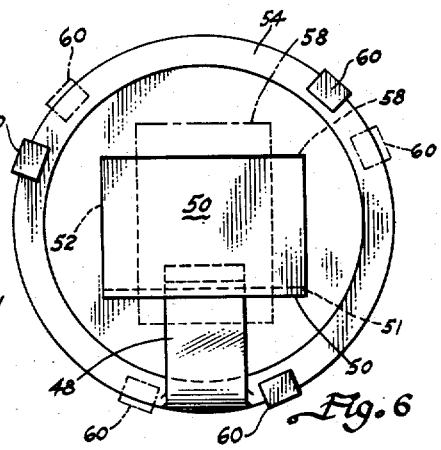

FIG. 6 is a front view of the film holder and target embodiment shown in FIG. 5 and illustrating, in full lines, one position of the principal shield means relative to the aiming element, while in broken lines, another position of the shield means relative to the aiming element is illustrated.

Figure 7:
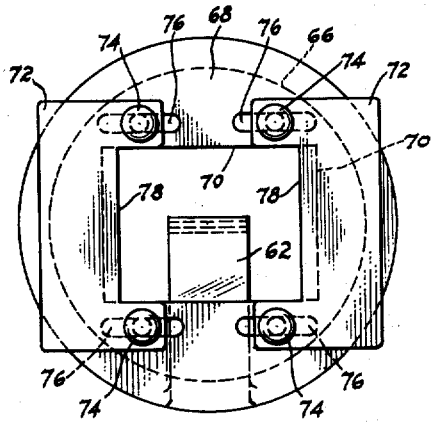

FIG. 7 is a front view of the aiming element portion of still another embodiment of film holder and aiming element embodying the principles of the present invention, said embodiment providing additional shield members adjustably supported relative to the aiming element and principal shield means, whereby the opening in the aiming element may be varied so as to restrict the area of X-rays discharged through said opening of the composite shield arrangement.

Figure 8:
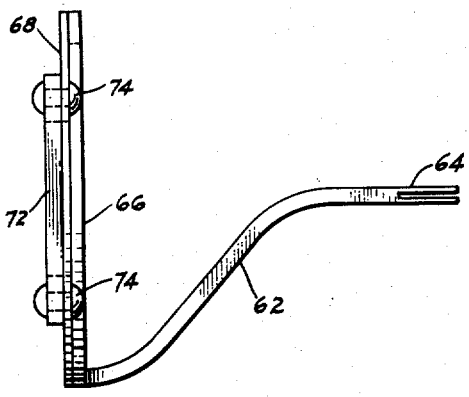

FIG. 8 is a side elevation of the embodiment of film holder and aiming element shown in FIG. 7.

Figure 9:
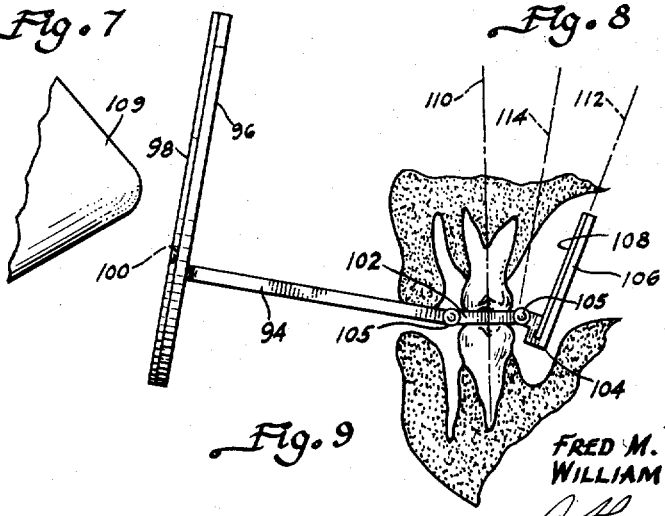

FIG. 9 is a side elevation of still another embodiment of combination film holder and aiming element illustrated as being positioned between a fragmentarily illustrated upper and lower posterior jaw section of a human face, this embodiment being adapted to hold a periapical type of X-ray film for use in accordance with a specific type of technique described hereinafter in the specification.

The X-ray film holder and aiming element comprising the present invention is of the type intended to be held between the teeth of a patient whose gums and/or teeth are to be X-rayed. By referring to FIG. 1, it will be seen that one embodiment of X-ray film holder and aiming element made in accordance with the present invention comprises a support member 10 which may be formed from any suitable material, other than lead, and is substantially strip-like as more readily can be seen from FIG. 2. Either connected to one end of the support member 10, or formed integrally therewith, is a preferably circular *aiming element* [target] 12. The area and shape of the aiming element 12 respectively are at least as great as and similar to the shape of the area of discharge of X-rays from the cone of a conventional X-ray machine, regardless of whether the cone is a long type or a pointed, short type. In FIG. 1, the fragmentary outer end of a long cone 14 is shown adjacent the aiming element 12.

If desired, the support member 10 and aiming element 12 may be molded integrally from suitable resin such as a synthetic polyamide (nylon) or methylmethacrylate. The end of the support member 10 opposite that which is connected to *aiming element* [target] 12 is provided with support means 16 for holding an X-ray film 18 within the oral cavity 20. In the particular illustration shown in FIG. 1, the support member 10 is clampingly held between opposed front or posterior teeth 22 of a patient, said teeth engaging the support member 10 adjacent the support means 16.

In this specifically illustrated embodiment of film holder and *aiming element* [target], support means 16 is arranged to hold the wings 24 of the X-ray film 18 which is of the type known in the dental profession as a bite-wing film. Said wings comprise stiff paper which readily may be inserted frictionally within the slot 26 of support means 16 for the X-ray film. Further, the curvature of the support member 10 is such that the rear portion, particularly, of said support member is substantially perpendicular to the plane of the aiming element 12 and is coaxial with the center of target 12.

Mounted upon what is regarded as the forward face of the aiming element 12 is a principal shield member or means 28. Preferably, the same is a relatively thin sheet of lead and is coextensive in area to and similar in shape to the *aiming element* [target] 12. Any suitable means such as an appropriate cement may be used to unite the shield member 28 with the aiming element 12. As is best seen from FIG. 2, the shield member 28 has an opening 30 therein which, in accordance with the preferred construction of the invention, is rectangular and has an area equal to or slightly less than that of a conventional X-ray film, either of the bitewing type illustrated in FIG. 1, or the periapical type which will be described hereinafter in conjunction with some of the other figures and embodiments of the invention.

Preferably, the size and area of the shield member 28 is at least coextensive with the cross-sectional area of the long blunt cone 14, of conventional size. Accordingly, any stray or random X-rays which tend to project or deflect outwardly from the main stream of X-rays being directed through the cone to the X-ray film will encounter the shield member 28 and be absorbed thereby, thus not reaching any tissues of the patient. It is only the X-rays which will be projected through the opening 30 of the shield member that will contact the tissues, bone and tooth structures of the patient.

Referring to FIG. 3, it will be seen that the embodiment illustrated therein comprises a support member 32 which is generally similar in shape to support member 10 of the embodiment shown in FIG. 1 except that the straight portion 34 thereof is not coaxial with the center of the *aiming element* [target] member 36 which is similar in size, shape and material to the *aiming element* [target] member 12 of the embodiment of FIG. 1. The curved end of support member 32 is fixed suitably to the aiming element member 36, as in regard to the embodiment shown in FIG. 1, and a principal shield member or means 38, preferably formed from thin sheet lead stock, is coextensive in size and shape with the aiming element member 36 and is fixed thereto suitably. The aiming element member 38 also has a preferably rectangular opening 40 therethrough to afford passage of X-rays therethrough within a limited area, as in regard to the opening 30 in the embodiment of FIG. 1.

The principal difference between the embodiment shown in FIG. 3 over that shown in FIG. 1 is that the rear end portion 34 of the embodiment in FIG. 3 has film support means 42 thereon which comprises a [vertical] *horizontal* groove 43 arranged to receive one edge of a periapical type of X-ray film 44. Further, a support member 46, which may comprise also an additional shield member if it includes a rectangular sheet of lead laminated therewith, extends vertically to portion 34 of member 32 and away from the groove 43. Preferably member 46 is at least co-extensive in area with the X-ray film 44. By such arrangement, in the event any X-rays happen to be projected entirely through the film 44, they will not be transmitted past the additional shield 46, whereby no tissues or other human substance in back of the film 44 will be contacted by the X-rays.

In FIG. 4, a fragmentary portion of an exemplary human face is shown in side elevation as for example when certain of the rear or posterior teeth of a patient are being X-rayed. In FIG. 4, the bitewing embodiment of film holder and aiming element illustrated in FIGS. 1 and 2 is shown. Said view affords an appreciation of how the front surface or face of the composite aiming element and shield end of the film holder and aiming element unit of said embodiment appears to a dentist or a technician incident to sighting the cone of an X-ray machine relative to the target. It will be understood that the film is substantially coextensive in shape and size with the opening 30 in the shield member 28.

Still another embodiment of the invention is illustrated in FIGS. 5 and 6 which respectively show the same in side elevation and front view. Most X-ray film is rectangular in size. The openings in the principal shield member, therefore, correspondingly is made rectangular in shape. The X-ray film usually is used with its longitudinal axis disposed horizontally such as shown in full lines in FIG. 6 when X-raying posterior teeth but when anterior teeth are X-rayed, the film is supported vertically and, correspondingly, the position of the rectangular opening in the shield should coincide with that of the film. Under the foregoing circumstances, the embodiment shown in FIGS. 5 and 6 is exemplary as far as the support member 48 and support means 50 are concerned, those selected for illustration in FIGS. 5 and 6 being substantially the same as those in FIG. 3. Thus, a periapical type of film 52 is shown mounted within groove 51 of support means 50.

The target 54 is fixed to one end of support member 48 and preferably is made from the same material as said support member, for example, a suitable synthetic resin such as methylmethacrylate or synthetic polyamide, or an appropriate metal such as aluminum. The principal shield member 56 has a rectangular opening 58 therein but, rather than being fixed to the aiming element member 54, as in regard to the preceding embodiments described hereinabove, shield member 56 is movable relative to aiming element member 54. Said shield member and aiming element preferably are circular, as shown in FIG. 6, and of substantially equal diameter. The shield member is arranged to be rotated about an axis perpendicular to and centrally of aiming element 54. Any suitable means may be utilized to maintain shield member 56 in rotatable relationship relative to the aiming element 54, such as a plurality of ears 60 which may be stamped relative to forming the shield member 56, so as to project radially from the perimeter of said shield member, and then said ears are bent over the peripheral edge of aiming element 54 and overlap the rear surface of said aiming element.

Preferably, only three ears 60 are utilized, particularly in order that there will be ample space between two adjacent ears to permit at least 90° of movement of the shield member arelative to the aiming element, without interfering with the support member 48. In fact, if the nearest edges of two adjacent ears 60 are spaced apart a distance equal to 90° of the circumference of shield 56, plus the width of support member 48, said pair of ears then may function as suitable stops to limit the rotation of the shield member relative to the target, as well as accurately position the longitudinal axis of opening 58 in the shield member either vertically or horizontally so as to afford either a relatively wide or narrow exposure in th horizontal direction when the film holder and aiming element of this embodiment is in use.

One further embodiment of the invention is illustrated in FIGS. 7 and 8, wherein means are provided for varying the size of the opening in the shield member in at least one direction. In this embodiment, the support member 62 and support means 64 are similar to the corresponding elements in the embodiments shown in FIGS. 1 and 6. The aiming element 66 supports shield member 68 comprising a sheet of lead having a preferably rectangular opening 70 therein.

In order to permit adjustability in one dimension such as the width of the shield opening 70 in a horizontal direction as viewed in FIG. 7, this embodiment of the invention includes the use of additional shield members 72 which are substantially U-shaped as seen in FIG. 7 and are slidable relative to the outer surface of shield member 68 which is designated as the principal shield member. Any suitable supporting means which will permit slidable movement of the additional shield members 72 relative to principal shield member 68 may be used. Exemplary means for such purposes, such as are illustrated in FIGS. 7 and 8, comprise headed rivets 74 which extend through suitable holes in additional shield members 72 and slots 76 in principal shield member 68. It thus will be seen that the inner edges 78 of said additional shield members 72 will control the opposite side edges of the openings 70 of said composite shield structure, whereby the width of said opening in a horizontal direction may be varied to a very substantial extent.

The embodiment of the invention shown in FIGS. 7 and 8 is particularly advantageous relative to X-raying teeth and intra-oral tissues of young children in order that, for example, in the event only one or two teeth are to be X-rayed, the field or the area of discharge from the cone of the X-ray machine may be restricted quite definitely to substantially only the matter desired to be X-rayed. Other tissues and intra-oral substances surrounding the subject to be X-rayed will not be subjected to contact by X-rays.

Still another embodiment of the invention is shown in FIG. 9, wherein the support member 94 extends preferably substantially perpendicularly from the rear surface of aiming element 96 which, in this embodiment, may be a disc or a flat ring. A shield member 98 having, for example, a rectangular opening 100 therein as in certain of the preceding embodiments, is fixed suitably to the aiming element 96. Preferably, the support member 94 engages the aiming element 96 adjacent the lower edge of opening 100.

The opposite end of support member 94 comprises a short extension or portion 102 which is pivotally connected to member 94 by a hinge 95 and is engaged between opposed upper and lower posterior or anterior teeth of a patient to support the inner end of the support member 94 within the oral cavity. Connected pivotally by another hinge 95 to the innermost end of the portion 102 is support means 104 and extending upwardly therefrom is a support member 106 which, if including a lead sheet, may comprise an additional shield, and aids in positioning the film 108 relative to the support means 104. The hinges 95 at opposite ends of portion 102 preferably are of a friction type so as to maintain desired adjusted relative positions of the connected elements as determined by the operator. This embodiment of the invention is used to practice the X-ray technique known as bisecting-the-angle, which usually is practiced with an X-ray machine having a short, pointed cone 109.

In order to understand said technique more readily, reference is made to certain exemplary lines and angles appearing in FIG. 9. For example, line 110 is coaxial with the longitudinal axis of the tooth to be X-rayed. Line 112 is parallel to the plane of the film 108. Lines 110 and 112 define an acute angle. Line 114 bisects said acute angle and is parallel to the plane of target 96. Hence, when film 108 is resting against support member 106, it will be accurately positioned within the support means 104 relative to target 96, whereby the dentist may accurately sight the cone of the X-ray machine relative to the target 96 and, when so sighted, the image projected upon the film 108 will be in true proportion to the slight foreshortening which occurs as a result of the target 96 not being parallel to the axis of the tooth but, rather, parallel to the bisector of the angle between the axis of the tooth and the plane of the film. Bisecting-the-angle technique preferably is practiced with a short pointed cone type of X-ray machine.

In all of the embodiments illustrated in the drawings and described hereinabove, holding means respectively to accommodate bitewing type of films and periapical type of films have been selected arbitrarily in certain instances in order to minimize the number of figures and illustrations to be required otherwise. It is to be understood that where holding means for bitewing film have been shown, the invention also is applicable to film holder and target embodiments having holding means to accommodate periapical types of X-ray film. Also, the material from which the various supporting members of the different embodiments are formed preferably are such as not to injure the teeth of patients when said supporting members are gripped between opposing upper and lower teeth of the patient and this contemplated support of the film holder and target embodiments by such gripping between the teeth affords firm support for the film holder and target while in use. To facilitate the taking of X-rays of molar teeth and especially third molars, it would be convenient to provide a U-shaped lateral offset in the various supporting members 10, 48, 62 and 94 intermediate of the ends thereof to accommodate the lip tissues and provide greater comfort to the patient.

*Inasmuch as the various embodiments of aiming elements and X-ray shields are co-extensive at the peripheries, it is apparent that such aiming elements and X-ray shields of the various embodiments which are fixed together for use are each combination aiming elements and X-ray shield means.*

From the foregoing, it will be seen that a number of different but related embodiments of the invention have been illustrated for purposes of minimizing excess and unnecessary exposure of human tissue to X-rays and particularly stray X-rays in conjunction with the taking of dental X-rays. The various embodiments are relatively simple yet highly effective, coupled with ease of use, to provide clear and sharp X-ray images upon conventional X-ray film of various types commonly used at present. Also, while the various embodiments of the invention incorporate certain basic concepts in each of the embodiments, they are not to be regarded as the equivalent of each other since each of the embodiments offer certain advantages not necessarily present in other embodiments.

While the invention has been described and illustrated in its several preferred embodiments, it should be understood that the invention is not to be limited to the precise details herein illustrated and described since the same may be carried out in other ways falling within the scope of the invention as claimed.

We claim:

1. An X-ray film holder and aiming element comprising a support member arranged to be positioned at one end within the oral cavity of a patient and provided on said end with support means to receive an X-ray film and hold it substantially transversely to said support member, an aiming element on the opposite end of said support member positioned transversely to said member and arranged to aid in sighting the cone of an X-ray machine concentrically with a film when supported by said support means, and X-ray shield means substantially equal in area and shape to that defined by the perimeter of the cone of a normal X-ray machine and carried by said support member adjacent said aiming element, said shield means having an opening therethrough of a similar shape and area to that of a conventional X-ray film and positioned so that a line passing perpendicularly through the center of said opening also will pass substantially through the center of said film, whereby scattering of X-rays emanating from said cone when in use and contacting the patient with scattered X-rays will be minimized.

2. The X-ray film holder and aiming element set forth in claim 1 further characterized by said aiming element and shield being substantially coextensive in area.

3. The X-ray film holder and [target] *aiming element* set forth in claim 1 further characterized by said aiming element comprising an endless rim of suitable circumference to enclose an area at least equal to the cross-sectional area of the cone of an X-ray machine, and said shield comprising a sheet of lead extending across said aiming element and connected thereto for support thereby.

4. The X-ray film holder and aiming element set forth in claim 1 further characterized by the center of said aiming element being substantially coaxial with the center of an X-ray film when mounted upon said support means and the opening in said shield means being substantially central of said aiming element.

5. An X-ray film holder and aiming element comprising a support arranged to be positioned at one end within the oral cavity of a patient and provided on said end with support means to receive an X-ray film and hold it substantially transversely to said support member, an aiming element on the opposite end of said support member positioned transversely to said member and arranged to aid in sighting the cone of an X-ray machine concentrically with a film when supported by said support means, and X-ray shield means at least equal in area to that of the cone of a normal X-ray machine carried by said support member adjacent said aiming element and having an opening therethrough of an area of predetermined size and shape substantially the same as that of a conventional X-ray film, and additional shield members movable relative to said shield means adjacent said opening therein and operable to variably diminish the open area thereof as desired, whereby scattering of X-rays emanating from said cone when in use and contacting the patient with scattered X-rays will be minimized and maximum clarity of the film image will result.

6. The X-ray film holder and [target] *aiming element* set forth in claim 5 further characterized by said shield means being a flat sheet and said additional shield members being slidably supported by said shield means.

7. An X-ray film holder and aiming element comprising a support member arranged to be positioned at one end within the oral cavity of a patient and provided on said end with support means to receive a rectangular X-ray film and hold it substantially transversely to said support member with its major axis either vertically or transversley relative to said support member, a susbtantially planar aiming element on the opposite end of said support member positioned transversely to said member and arranged to aid in sighting the cone of an X-ray machine concentrically with a film when supported by said support means, and X-ray shield means at least equal in area to that of the cone of a normal X-ray machine rotatably supported by said aiming element for movement about an axis transverse to the plane of said aiming element, said shield means being provided with a rectangular opening therethrough having an area and shape approximately equal to that of a conventional X-ray film, whereby scattering of X-rays emanating from said cone when in use and contact of the patient by scattered X-rays will be minimized and the axes of said opening in said shield may be oriented relative to the corresponding axes of said rectangular X-ray film when supported by said support means.

8. The X-ray film holder and aiming element set forth in claim 7 further characterized by said aiming element and shield being circular and coaxial.

9. The X-ray film holder and aiming element set forth in claim 1 further characterized by said support member being connected at one end to and extending substantially perpendicularly to said aiming element and the other end portion of said support member being disposed at a slight angle to said member, and support means connected to the outer end of said other end portion of said support member and extending away therefrom at a slight angle away from a plane extending perpendicularly to said other end portion of said support member, whereby said aiming element may be aimed at by the cone of an X-ray machine to practice the bisect-the-angle technique and thereby minimize distortion of the X-ray film image from the true shape and size of a tooth being X-rayed.

10. The X-ray holder set forth in claim 9 further characterized by the opposite ends of said other end portion of said support member being adjustably pivotally connected respectively to said support member and support means, whereby the angularity of said support means relative to said aiming element and support member may be adjusted as desired.

11. An X-ray film holder and aiming element comprising a support member arranged to be positioned at one end within the oral cavity of a patient and provided on said end with means to hold an X-ray film substantially transversely of said support means, an aiming element on the opposite end of said support member positioned transversely thereto and arranged to aid in sighting the cone of an X-ray machine concentrically with a film when supported by said film holding means, X-ray shield means at least equal in area to that of the cone of a conventional X-ray machine carried by said support member adjacent said aiming element and provided with an opening therethrough substantially the same shape and size as that of a conventional X-ray film, and combined additional shield and support means on said one end of said support member adjacent said film holding means and disposed adjacent the back of an X-ray film when mounted upon said film holding means, whereby scattering of X-rays emanating from said cone and contacting of the patient by said scattered X-rays or X-rays passing through X-ray film will be minimized.

*12. An X-ray film holder and aiming element comprising a support member arranged to be positioned at one end within the oral cavity of a patient and provided on said end with support means to receive an X-ray film and hold it substantially transversely to said support member, a combined aiming element and X-ray shield means on the opposite end of the support member having an area and shape at least substantially equal to that of the perimeter of the X-ray cone with which the same is used and positioned transversely to said member and arranged to aid in sighting the cone of an X-ray machine concentrically with the film when supported by said support means, said combined aiming element and X-ray shield means having an opening therethrough of a substantially similar shape and area to that of a conventional X-ray film and positioned so that a line passing perpendicularly through the center of said opening also will pass substantially through the center of said film, whereby the patient will be shielded from unnecessary primary radiation and from at least most of the scattered radiation from said cone when in use.*

*13. The X-ray film holder and aiming element set forth in claim 12 further characterized by said support member being connected to said combined aiming element and X-ray shield means adjacent one edge thereof and extending rearwardly transversely to the plane thereof and inwardly toward the central perpendicular axis of said combined element and means for connection to said X-ray support means.*

References Cited by the Examiner

The following references, cited by the Examiner, are of record in the patented file of this patent or the original patent.

UNITED STATES PATENTS

| | | | |
|---|---|---|---|
| 1,947,014 | 2/34 | Levy | 250—70 X |
| 2,090,933 | 8/37 | Bolin | 250—70 X |
| 2,382,484 | 8/45 | Homer | 250—64 |
| 2,612,609 | 9/52 | Bowser | 250—70 |
| 2,777,068 | 1/57 | Bowser | 250—70 X |

RALPH G. NILSON, *Primary Examiner.*